United States Patent [19]

Bailey et al.

[11] 4,024,164

[45] May 17, 1977

[54] 2-(2-BENZOXYETHOXY)-ETHYL-2-FUROATE

[75] Inventors: August V. Bailey; Gordon J. Boudreaux; Gene Sumrell, all of New Orleans; Arthur F. Novak, Baton Rouge, all of La.

[73] Assignee: The United States of America as represented by the Secretary of Agriculture, Washington, D.C.

[22] Filed: Mar. 15, 1976

[21] Appl. No.: 667,055

[52] U.S. Cl. .............................................. 260/347.5
[51] Int. Cl.$^2$ ........................................ C07D 307/68
[58] Field of Search ................................ 260/347.5

[56] References Cited

UNITED STATES PATENTS 3,770,813  11/1973  Kollar .................... 260/347.5 X

*Primary Examiner*—Henry R. Jiles
*Assistant Examiner*—Bernard Dentz
*Attorney, Agent, or Firm*—M. Howard Silverstein; David G. McConnell; Salvador J. Cangemi

[57] ABSTRACT

New mixed esters of diols having one hydroxyl group esterified with benzoic acid and the other esterified with various saturated or unsaturated aliphatic acids or aromatic acids other than benzoic are found to have antimicrobial activity against several pathogenic microorganisms, and to have properties making them useful as antimicrobial agents.

1 Claim, No Drawings

2-(2-BENZOXYETHOXY)-ETHYL-2-FUROATE

This invention relates to certain new organic esters. More particularly, this invention relates to mixed diesters of aliphatic diols which exhibit antimicrobial activity. The mixed esters which are the subject of this invention are characterized by the fact that as growth inhibitors, they are effective against a variety of microorganisms that includes bacteria, yeasts, and molds. Some of these esters exhibit broad antimicrobial spectrum, whereas others exhibit selective antimicrobial spectrum.

The compounds which are the subject of this invention are:

2-benzoxyethyl laurate, $C_6H_5COOCH_2CH_2OCOC_{11}H_{23}$ 2-benzoxyethyl palmitate, $C_6H_5COOCH_2CH_2OCOC_{15}H_{31}$ 2-benzoxyethyl oleate, $C_6H_5COOCH_2CH_2OCOC_{17}H_{33}$ 2-benzoxyethyl erucate, $C_6H_5COOCH_2CH_2OCOC_{21}H_{41}$ 2-benzoxyethyl 12-acetoxyoleate, $C_6H_5COOCH_2CH_2OCO(CH_2)_7CH=CHCH_2CH(OCOCH_3)(CH_2)_5CH_3$ 2-benzoxyethoxyethyl furoate,

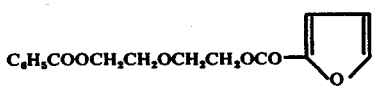

2-benzoxyethoxyethyl p-toluate,

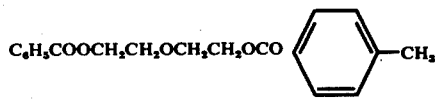

2-benzoxyethoxyethyl trimethylacetate, $C_6H_5COOCH_2CH_2OCH_2CH_2OCOC(CH_3)_3$ 2-benzoxyethoxyethyl laurate, $C_6H_5COOCH_2CH_2OCH_2CH_2OCOC_{11}H_{23}$ 2-benzoxyethoxyethyl palmitate, $C_6H_5COOCH_2CH_2OCH_2CH_2OCOC_{15}H_{31}$ 2-benzoxyethoxyethyl oleate, $C_6H_5COOCH_2CH_2OCH_2CH_2OCOC_{17}H_{33}$ 2-benzoxyethoxyethyl erucate, $C_6H_5COOCH_2CH_2OCH_2CH_2OCOC_{21}H_{41}$ 2-benzoxyethoxyethyl 12-acetoxyoleate, $C_6H_5COOCH_2CH_2OCH_2CH_2OCO(CH_2)_7CH=CHCH_2CH(OCOCH_3)(CH_2)_5CH_3$ 4-benzoxy-2-butenyl laurate, $C_6H_5COOCH_2CH=CHCH_2OCOC_{11}H_{23}$ 4-benzoxy-2-butenyl palmitate, $C_6H_5COOCH_2CH=CHCH_2OCOC_{15}H_{31}$ 4-benzoxy-2-butenyl oleate, $C_6H_5COOCH_2CH=CHCH_2OCOC_{17}H_{33}$ 4-benzoxy-2-butenyl erucate, $C_6H_5COOCH_2CH=CHCH_2OCOC_{21}H_{41}$ 4-benzoxy-2-butenyl trimethylacetate, $C_6H_5COOCH_2CH=CHCH_2OCOC(CH_3)_3$ 4-benzoxy-2-butenyl hydrocinnamate, $C_6H_5COOCH_2CH=CHCH_2OCOCH_2CH_2C_6H_5$ The new esters which are the subject of this invention were prepared by conventional methods.

The bioactivity of these various new compounds has been established in vitro but, as will be apparent to those skilled in the arts pertaining to the growth inhibition of bacteria, yeast, and molds, the compounds, besides being used as such, will for utilitarian purposes commonly be formulated using a diluent that can be either liquid, viscous, or solid.

A wide variety of extending agents is operable, the only significant requirement being that the diluent or extender be inert with respect to the ester involved. Petroleum jellies, various alcohols and polyols, vegetable oils and the like are suitable.

In the case of intended use as fungicide in the protective coating composition art, the compounds that are the subject of this invention are compatible with conventional and with drying oil modified alkyds, for example. These new compounds are compatible with various resins, such as polyvinyl chloride, for example, and can serve as both plasticizer and antifungal agent for such materials.

Specific examples showing the preparation of each of the new compounds being claimed are set forth below along with appropriate data in tabular form which is being submitted for the purpose of establishing the growth inhibiting properties of the claimed compounds.

The microorganisms used were obtained from stock cultures. Difco Dehydrated Mycological Agar at pH 7.0 was used to test the inhibition of the test organisms by the compounds.

The esters were screened for their antimicrobial activity against two bacteria — a gram positive, *Staphylococcus aureus*, and a gram negative, *Escherichia coli*; a yeast, *Torula sp.*; and three pathogenic molds, *Candida albicans*, *Aspergillus flavus*, and *Asperigillus sp.*

Seeded agar plates were used to measure the antimicrobial activity against bacteria and the yeast. Poured agar plates were used to measure the antimicrobial activity against the molds. The poured agar plates were prepared by pouring dilutions of mold spores over the hardened agar plates.

Filter paper discs 6.5 mm in diameter, made from Whatman Number 1 filter paper were wetted until they were completely saturated with the compounds being tested, and the wetted discs were placed on the surface of the agar plates inoculated with the test organisms.

To eliminate any errors which could result from an insufficient number of tests, a minimum of three experiments, at different times, employing duplicate plates were made for each compound under test.

All test plates were incubated at the optimum growing temperature for each organism and readings were taken after 24, 48, 72, and 120 hour periods. The results are tabulated in Table I.

TABLE I

ANTIMICROBIAL ACTIVITY OF SOME DIESTERS OF ALIPHATIC DIOLS

| Compound | Antimicrobial Activity[a] | | | | | |
|---|---|---|---|---|---|---|
| | Candida albicans | Staphylococcus aureus | Escherichia coli | Aspergillus sp. | Torula sp. | Aspergillus flavis |
| 1. 2-Benzoyloxyethyl laurate | ++ | ++ | + | ++ | — | — |
| 2. 2-Benzoyloxyethyl palmitate | + | 00 | + | 00 | — | — |
| 3. 2-Benzoyloxyethyl oleate | ++ | ++ | + | ++ | — | — |
| 4. 2-Benzoyloxyethyl erucate | 00 | 0 | 00 | 00 | — | — |
| 5. 2-Benzoyloxyethyl 12-acetoxyoleate | 00 | 0 | 00 | 00 | — | — |
| 6. 2-Benzoyloxyethoxyethyl furoate | 00 | 00 | 00 | + | — | — |
| 7. 2-Benzoyloxyethoxyethyl p-toluoate | 00 | + | 0 | 00 | — | — |
| 8. 2-Benzoyloxyethoxyethyl trimethylacetate | — | + | 00 | — | 00 | + |
| 9. 2-Benzoyloxyethoxyethyl laurate | 0 | 00 | 00 | 00 | — | — |
| 10. 2-Benzyloxyethoxyethyl palmitate | — | 00 | 00 | 0 | 0 | — |
| 11. 2-Benzoyloxyethoxyethyl oleate | 00 | 0 | 00 | 00 | — | — |
| 12. 2-Benzoyloxyethoxyethyl erucate | + | + | 00 | + | — | — |
| 13. 2-Benzoyloxyethoxyethyl 12-acetoxyoleate | 30 | 00 | 00 | 00 | — | — |
| 14. 4-Benzoyloxy-2-butenyl laurate | — | ++ | ++ | — | ++ | 0 |
| 15. 4-Benzyloxy-2-butenyl palmitate | — | + | 0 | 0 | + | — |
| 16. 4-Benzyloxy-2-butenyl oleate | — | ++ | 0 | + | ++ | — |
| 17. 4-Benzyloxy-2-butenyl erucate | — | ++ | 0 | 0 | + | — |
| 18. 4-Benzyloxy-2-butenyl trimethylacetate | — | ++ | + | — | ++ | + |
| 19. 4-Benzyloxy-2-butenyl hydrocinnamate | — | ++ | 00 | — | + | 0 |

[a] ++ = The zone of inhibition was at least 0.5 cm beyond disc at 120 hr.
+ = The zone of inhibition was less than 0.5 cm beyond disc at 120 hr.
00 = Organism failed to grow on disc at 120 hr.
0 = Organism exhibited slight growth on the saturated disc at 120 hr.

EXAMPLE 1

2-Benzoyloxyethyl laurate

To 16 grams (0.1 mole) of ethylene glycol monobenzoate containing 20 gms (0.25 mole) of pyridine was added 22 gms (0.1 mole) of lauroyl chloride with stirring. With the final addition of lauroyl chloride approximately 50 ml of benzene was added and the mixture stirred for 1 hour. The pyridine hydrochloride was filtered off and the product water washed to remove residual pyridine. The benzene solution was dried over anhydrous sodium sulfate and percolated through a column filled with activated alumina to removal residual free acid. The solvent was removed at reduced pressure. The product, 2-benzoyloxyethyl laurate, was characterized on the basis of the chemical shifts in the NMR spectrum and the absence of OH-stretching and other bands associated with reaction byproducts or impurities.

EXAMPLE 2

2-Benzoyloxyethyl palmitate

2-Benzoyloxyethyl palmitate was prepared by the procedure of Example 1 from 16 grams (0.1 mole) of ethylene glycol monobenzoate and 26 gms (0.1 mole) of palmitoyl chloride. The structure of the final product was characterized on the basis of NMR and IR spectral analyses as described in Example 1.

EXAMPLE 3

2-Benzoyloxyethyl oleate

2-Benzoyloxyethyl oleate was prepared by the procedure of Example 1 from 16 gms (0.1 mole) of ethylene glycol monobenzoate and 30 gms (0.1 mole) of oleoyl chloride. The structure of the final product was characterized on the basis of NMR and IR spectral analyses as described in Example 1.

EXAMPLE 4

2-Benzoyloxyethyl erucate

2-Benzoyloxyethyl erucate was prepared by the procedure of Example 1 from 16 gms (0.1 mole) of ethylene glycol monobenzoate and 35.5 gms (0.1 mole) of erucoyl chloride. The structure of the final product was characterized on the basis of NMR and IR spectral analyses as described in Example 1.

EXAMPLE 5

2-Benzoyloxyethyl 12-acetoxyoleate

2-Benzoyloxyethyl 12-acetoxyoleate was prepared by the procedure of Example 1 from 16 gms (0.1 mole) of ethylene glycol monobenzoate and 36 gms (0.1 mole) of 12-acetoxyoleoyl chloride. The structure of the final product was characterized on the basis of NMR and IR spectral analyses as described in Example 1.

EXAMPLE 6

2-Benzoyloxyethoxyethyl furoate

2-Benzoyloxyethoxyethyl furoate was prepared by the procedure of Example 1 from 21 gms (0.1 mole) of diethylene glycol monobenzoate and 13 gms (0.1 mole) of furoyl chloride. The structure of the final product was characterized on the basis of NMR and IR spectral analyses as described in Example 1.

EXAMPLE 7

2-Benzoyloxyethoxyethyl p-toluoate

2-Benzoyloxyethoxyethyl p-toluoate was prepared by the procedure of Example 1 from 21 gms (0.1 mole) of diethylene glycol monobenzoate and 15 gms (0.1 mole) of toluoyl chloride. The structure of the final product was characterized on the basis of NMR and IR spectral analyses as described in Example 1.

EXAMPLE 8

2-Benzoyloxyethoxyethyl trimethylacetate

2-Benzoyloxyethoxyethyl trimethylacetate was prepared by the procedure of Example 1 from 21 gms (0.1 mole) of diethylene glycol monobenzoate and 12 gms (0.1 mole) of trimethylacetyl chloride. The structure of the final product was characterized on the basis of NMR and IR spectral analyses as described in Example 1.

EXAMPLE 9

2-Benzoyloxyethoxyethyl laurate

2-Benzoyloxyethoxyethyl laurate was prepared by the procedure of Example 1 from 21 gms (0.1 mole) of diethylene glycol monobenzoate and 22 gm (0.1 mole) of lauroyl chloride. The structure of the final product was characterized on the basis of NMR and IR spectral analyses as described in Example 1.

EXAMPLE 10

2-Benzoyloxyethoxyethyl palmitate

2-Benzoyloxyethoxyethyl palmitate was prepared by the procedure of Example 1 from 21 gms (0.1 mole) of diethylene glycol monobenzoate and 26 gms (0.1 mole) of palmitoyl chloride. The structure of the final product was characterized on the basis of NMR and IR spectral analyses as described in Example 1.

EXAMPLE 11

2-Benzoyloxyethoxyethyl oleate

2-Benzoyloxyethoxyethyl oleate was prepared by the procedure of Example 1 from 21 gms (0.1 mole) of diethylene glycol monobenzoate and 30 gms (0.1 mole) of oleoyl chloride. The structure of the final product was characterized on the basis of NMR and IR spectral analyses as described in Example 1.

EXAMPLE 12

2-Benzoyloxyethoxyethyl erucate

2-Benzoyloxyethoxyethyl erucate was prepared by the procedure of Example 1 from 21 gms (0.1 mole) of diethylene glycol monobenzoate and 35.5 gms (0.1 mole) of erucoyl chloride. The structure of the final product was characterized on the basis of NMR and IR spectral analyses as described in Example 1.

EXAMPLE 13

2-Benzoyloxyethoxyethyl 12-acetoxyoleate

2-Benzoyloxyethoxyethyl 12-acetoxyoleate was prepared by the procedure of Example 1 from 21 gms (0.1 mole) of diethylene glycol monobenzoate and 36 gms (0.1 mole) of 12-acetoxyoleoyl chloride. The structure of the final product was characterized on the basis of NMR and IR spectral analyses as described in Example 1.

EXAMPLE 14

4-Benzoyloxy-2-butenyl laurate

2-Benzoyloxy-2-butenoyl laurate was prepared by the procedure of Example 1 from 19 gms (0.1 mole) of 4-hydroxy-2-butenyl benzoate and 22 gms (0.1 mole) of lauroyl chloride. The structure of the final product was characterized on the basis of NMR and IR spectral analyses as described in Example 1.

EXAMPLE 15

4-Benzoyloxy-2-butenyl palmitate

4-Benzoyloxy-2-butenyl palmitate was prepared by the procedure of Example 1 from 19 gms (0.1 mole) of 4-hydroxy-2-butenyl benzoate and 26 gms (0.1 mole) of palmitoyl chloride. The structure of the final product was characterized on the basis of NMR and IR spectral analyses as described in Example 1.

EXAMPLE 16

4-Benzoyloxy-2-butenyl oleate

4-Benzoyloxy-2-butenyl oleate was prepared by the procedure of Example 1 from 19 gms (0.1 mole) of 4-hydroxy-2-butenyl benzoate and 30 gms (0.1 mole) of oleoyl chloride. The structure of the final product was characterized on the basis of NMR and IR spectral analyses as described in Example 1.

EXAMPLE 17

4-Benzoyloxy-2-butenyl erucate

4-Benzoyloxy-2-butenyl erucate was prepared by the procedure of Example 1 from 19 gms (0.1 mole) of 4-hydroxy-2-butenyl benzoate and 35.5 gms (0.1 mole) of erucoyl chloride. The structure of the final product was characterized on the basis of NMR and IR spectral analyses as described in Example 1.

EXAMPLE 18

4-Benzoyloxy-2-butenyl trimethylacetate

4-Benzoyloxy-2-butenyl trimethylacetate was prepared by the procedure of Example 1 from 19 gms (0.1 mole) of 4-hydroxy-2-butenyl benzoate and 12 gms (0.1 mole) of trimethylacetyl chloride. The structure of the final product was characterized on the basis of NMR and IR spectral analyses as described in Example 1.

EXAMPLE 19

4-Benzoyloxy-2-butenyl hydrocinnamate

4-Benzoyloxy-2-butenyl hydrocinnamate was prepared by the procedure of Example 1 from 19 gms. (0.1 mole) of 4-hydroxy-2-butenyl benzoate and 17 gms (0.1 mole) of hydrocinnamoyl chloride. The structure of the final product was characterized on the basis of NMR and IR spectral analyses as described in Example 1.

We claim:

1. 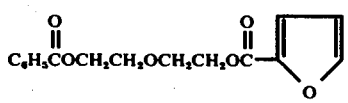

* * * * *